US00PP22655P2

(12) United States Plant Patent
Smith

(10) Patent No.: US PP22,655 P2
(45) Date of Patent: Apr. 17, 2012

(54) ***CHRYSANTHEMUM* PLANT NAMED 'SYNJAC PEAFUS'**

(50) Latin Name: *Chrysanthemum×morifolium*
Varietal Denomination: Synjac Peafus

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 32 days.

(21) Appl. No.: 12/925,281

(22) Filed: Oct. 18, 2010

(51) Int. Cl.
*A01H 5/00* (2006.01)

(52) U.S. Cl. ..... Plt./287

(58) Field of Classification Search ..... Plt./287, Plt./291
See application file for complete search history.

*Primary Examiner* — June Hwu
(74) *Attorney, Agent, or Firm* — S. Matthew Edwards

(57) ABSTRACT

A new *Chrysanthemum* plant named 'Synjac Peafus' particularly distinguished by the small to medium sized flowers with cream and coral two-toned colored ray florets, dark yellow-green foliage, uniform ball-shaped plant habit and a natural season flowering about mid-September.

1 Drawing Sheet

Latin name of the genus and species of the plant claimed: *Chrysanthemum×morifolium.*

Varietal denomination: 'Synjac Peafus'.

BACKGROUND OF THE NEW PLANT

The present invention comprises a new *Chrysanthemum*, botanically known as *Chrysanthemum×morifolium*, and hereinafter referred to by the variety name 'Synjac Peafus'.

'Synjac Peafus' is a product of a planned breeding program. The new cultivar has small to medium sized flowers with cream and coral two-toned colored ray florets, dark yellow-green foliage, uniform ball-shaped plant habit and a natural season flowering about mid-September.

'Synjac Peafus' originates as a natural whole plant mutation of 'Yojacqueline', U.S. Plant Pat. No. 18,927, and was discovered outdoor in a large quantity trial format and selected by the inventor as a single flowering plant within a population of the parent cultivar in a controlled breeding program in Alva, Fla. in November 2006. The parent cultivar 'Yojacqueline' has two-toned pink ray florets and has a flower color that fades less in the heat of summer.

The first act of asexual reproduction of 'Synjac Peafus' was accomplished when vegetative cuttings were propagated from the initial selection in December 2006 in a controlled environment in Alva, Fla.

BRIEF SUMMARY OF INVENTION

Horticultural examination of plants grown from cuttings of the plant initiated in December 2006, and continuing thereafter, has demonstrated that the combination of characteristics as herein disclosed for 'Synjac Peafus' are firmly fixed and are retained through successive generations of asexual reproduction.

'Synjac Peafus' has not been observed under all possible environmental conditions. The phenotype may vary significantly with variations in environment such as temperature, light intensity and day length.

A Plant Breeder's Right for this cultivar was applied for in Canada on Oct. 30, 2009 (09-6767). 'Synjac Peafus' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPH

The accompanying photographic drawing shows typical flower and foliage characteristics of 'Synjac Peafus' with colors being as true as possible with an illustration of this type. The photographic drawing shows a flowering potted plant of the new variety growing in a 9 inch pot in an outdoor trial in Monroeville, N.J. in September 2008. This plant is about 12 weeks old.

DETAILED BOTANICAL DESCRIPTION

The plant descriptions and measurements were taken in Gilroy, Calif. in the later summer 2009 under natural light. These plants used for the descriptions were about 10 weeks old.

Color references are made to The Royal Horticultural Society Colour Chart (R.H.S.) 2001.

TABLE 1

DIFFERENCES BETWEEN THE NEW VARIETY 'SYNJAC PEAFUS' AND A SIMILAR VARIETY

| | 'Synjac Peafus' | 'Gedi Two Cas' (U.S. Plant Pat. No. 14,428) |
|---|---|---|
| Flower size: | Smaller | Little larger |
| Flower color: | More intense, 2 toned | More faded, less intense |
| Disc floret quantity: | Fewer | More |
| Flowering response: | More uniform | Less uniform |

Plant:
*Form, growth and habit*.—Herbaceous decorative garden; stems upright and outwardly spreading, freely branching, strong and moderately vigorous growth habit.
*Plant height*.—About 10 cm.
*Plant height* (*inflorescence included*).—14-16 cm.
*Plant width*.—20 cm.
*Garden performance and tolerance to weather*.—Very good.

Roots:
*Number of days to initiate roots*.—About 4 days at about 22 degrees C.
*Number of days to produce a rooted cutting*.—10-12 days at 22 degrees C.
*Type*.—Fine; fibrous, free branching.
*Color*.—RHS N155B but whiter.

Foliage:
*Arrangement*.—Alternate, simple.
*Immature, leaf color, upper surface*.—RHS 147A.
*Lower surface*.—RHS 147B.
*Mature, leaf color, upper surface*.—RHS 147A.
*Lower surface*.—RHS 147B.
*Length*.—2.4-2.9 cm.
*Width*.—2.0-2.5 cm.
*Shape*.—Squat ovate.
*Base shape*.—Attenuate.
*Apex shape*.—Mucronulate.
*Margin*.—Palmately lobed; very slightly and irregularly serrulate.
*Texture, upper surface*.—Bifid T-shaped hairs.
*Lower surface*.—Bifid T-shaped hairs.
*Color of veins, upper surface*.—RHS 146B basally, otherwise indistinct.
*Color of veins, lower surface*.—RHS 146B basally, otherwise indistinct.
*Petiole color*.—RHS 146B.
*Length*.—0.5 cm.
*Diameter*.—0.15 cm.
*Texture*.—Bifid T-shaped hairs.

Stem:
*Quantity of main branches per plant*.—About 15.
*Color of stem*.—RHS 138B.
*Length of stem*.—7-9 cm.
*Diameter*.—0.3 cm.
*Length of internodes*.—0.5-1.0 cm.
*Texture*.—Bifid T-shaped hairs.
*Color of peduncle*.—RHS 138A.
*Length of peduncle*.—4.5-5.0 cm.
*Peduncle diameter*.—0.15 cm.
*Texture*.—Bifid T-shaped hairs.

Inflorescence:
*Type*.—Compositae type, solitary inflorescences (decorative-type) borne terminally above foliage, ray florets arranged acropetally on a capitulum.
*Natural season flowering*.—About mid-September.
*Quantity of inflorescences per plant*.—About 30 open with About 50 buds.
*Lastingness of individual blooms on the plant*.—3-4 weeks.
*Fragrance*.—Slightly spicy.

Bud (just when opening/showing color):
*Color*.—RHS 4A with RHS 52 B to RHS 52C apex.
*Length*.—0.7-1.0 cm.
*Width*.—1.0 cm.
*Shape*.—Oblate.

Immature inflorescence:
*Diameter*.—2.6-3.0 cm.
*Color of ray florets, upper surface*.—RHS 4B basally with RHS 52 B to RHS 52C apex.
*Lower surface*.—RHS 4D with RHS 52 C apex.

Mature inflorescence:
*Diameter*.—3.4-3.6 cm.
*Depth*.—1.6-1.7 cm.
*Total diameter of 'disc'*.—0.1 cm but almost indistinct.
*Receptacle height*.—0.3-0.4 cm.
Receptacle diameter.—0.3-0.4 cm.

Ray florets:
*Average quantity of florets*.—About 130-140 in numerous whorls.
*Color of florets, upper surface*.—RHS 4C basally with RHS 52C to RHS 52D apex.
*Lower surface*.—RHS 4D with RHS 52C apex.
*Length* (*cm*).—1.8-1.9 cm.
*Width* (*cm*).—0.45 cm.
*Shape*.—Elliptical.
*Apex shape*.—Praemorse.
*Margin*.—Entire.
*Texture, upper surface*.—Papillose.
*Lower surface*.—Papillose.

Disc florets:
*Average quantity of florets*.—1-2.
*Color of florets*.—RHS 1A.
*Length*.—0.4 cm.
*Width*.—0.1 cm.
*Shape*.—Tubular, elongated.
*Apex shape*.—Acute, 5 pointed.

Phyllaries:
*Quantity*.—About 35.
*Color, upper surface*.—RHS 146C.
*Lower surface*.—RHS 146B.
*Length*.—0.5-0.7 cm.
*Width*.—0.1-0.2 cm.
*Shape*.—Ovate to lanceolate.
*Apex shape*.—Acute.
*Based*.—Fused.
*Margins*.—Entire.
*Texture, upper surface*.—Glabrous.
*Lower surface*.—Bifid T-shaped hairs.

Reproductive organs:
*Pistil*.—1.
*Found on both florets*.—Yes.
*Length*.—0.4 cm.
*Style color*.—RHS 1B.
*Style length*.—0.3 cm.
*Stigma color*.—RHS 2B.
*Stigma shape*.—Bi-parted.
*Ovary color*.—RHS 155C.
*Stamens*.—1.
*Found on disc florets only*.—Yes.
*Color of filaments*.—RHS 1C.
*Length filaments*.—0.3 cm.
*Anther color*.—RHS 3B.
*Anther length*.—0.15 cm.
*Anther shape*.—Oblong.

*Color of pollen*.—RHS 5B.

*Pollen amount*.—Moderate.

*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'Synjac Peafus' substantially as illustrated and described herein.

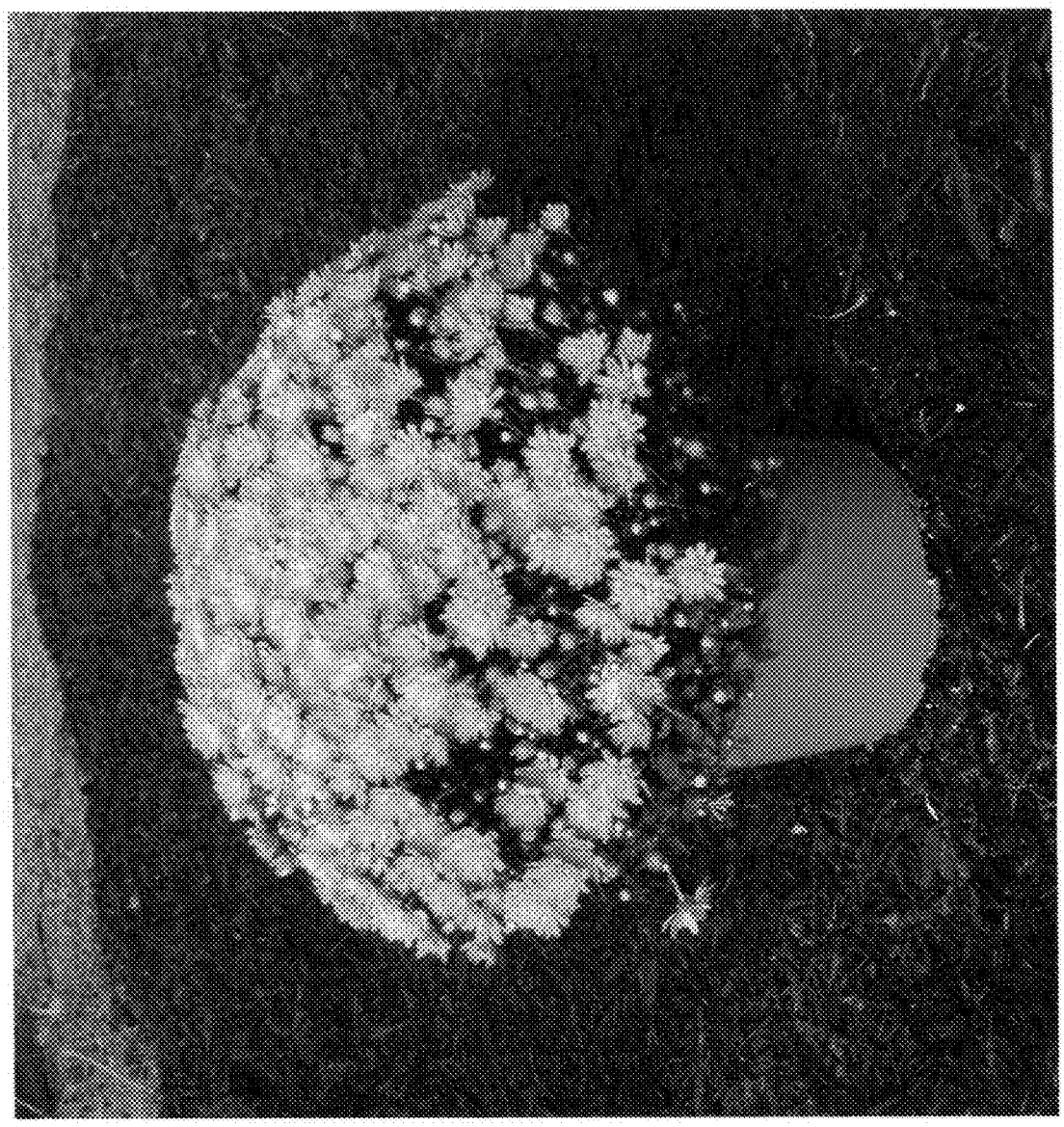

* * * * *